United States Patent [19]

Ishimaru et al.

[11] Patent Number: 5,028,433
[45] Date of Patent: Jul. 2, 1991

[54] READILY ABSORBABLE DRUG FORMULATION OF NB-818

[75] Inventors: Sueaki Ishimaru; Kiyohisa Ouchi; Kimito Takeuchi; Masaki Yamada, all of Menuma, Japan

[73] Assignee: Banyu Pharmaceutical Co., Ltd., Tokyo, Japan

[21] Appl. No.: 440,276

[22] Filed: Nov. 22, 1989

[30] Foreign Application Priority Data

Nov. 30, 1988 [JP] Japan ................. 63-303699

[51] Int. Cl.⁵ ............................................. A61K 9/20
[52] U.S. Cl. .................................. 424/464; 424/465; 424/470; 424/490; 424/489; 424/494; 424/497; 424/80; 424/81
[58] Field of Search ............... 424/464, 470, 490, 489, 424/494, 497, 80, 465

[56] References Cited

U.S. PATENT DOCUMENTS

| 4,267,138 | 5/1981 | Dobo et al. ............ | 424/494 |
| 4,695,467 | 9/1987 | Uemura et al. ........ | 424/489 |
| 4,765,990 | 8/1988 | Sugimoto et al. ..... | 424/494 |
| 4,772,475 | 9/1988 | Fukui et al. ........... | 424/470 |
| 4,840,799 | 6/1989 | Appelgren et al. .... | 424/490 |
| 4,849,227 | 7/1989 | Cho ...................... | 424/490 |
| 4,851,233 | 7/1989 | Khan et al. ........... | 424/470 |
| 4,880,623 | 11/1989 | Piergiorgio et al. ... | 424/470 |
| 4,882,167 | 11/1989 | Jang ..................... | 424/470 |
| 4,898,736 | 2/1990 | Katdare ................. | 424/470 |

FOREIGN PATENT DOCUMENTS 0001247 4/1979 European Pat. Off. .
0301133 1/1989 European Pat. Off. .

OTHER PUBLICATIONS

STN International Information Services Data Base; Chemical Abstracts, Accession No. 102, No. 13, Banyu Pharmaceutical Co., Ltd.

*Primary Examiner*—Thurman K. Page
*Assistant Examiner*—James M. Spear
*Attorney, Agent, or Firm*—Oblon, Spivak, McClelland, Maier & Neustadt

[57] ABSTRACT

A readily absorbable drug formulation obtained by incorporating to a water-soluble or enteric polymer, both a nonionic surfactant and (±)-2-carbamoyloxymethyl-4- (2,3-dichlorophenyl)-6-methyl-1,4-dihydropyrodine-3,5-dicarboxylic acid 3-isopropyl ester 5-methyl ester or (−)-2-carbamoyloxymethyl-4-(2,3-dichlorophenyl)-6-methyl-1,4-dihydropyridine-3,5-dicarboxylic acid 3-isopropyl ester 5-methyl ester.

9 Claims, 5 Drawing Sheets

FIGURE 5

READILY ABSORBABLE DRUG FORMULATION OF NB-818

The present invention is useful in the pharmaceutical field. More particularly, it relates to a readily absorbable drug formulation of NB-818 [(±)-2-carbamoyloxymethyl-4-(2,3-dichlorophenyl)-6-methyl-1,4-dihydropyridine-3,5-dicarboxylic acid 3-isopropyl ester -methyl ester]or NB-818 optical isomer [(-)-2-carbamoyloxymethyl-4-(2,3-dichlorophenyl)-6-methyl-1,4-dihydropyridine-3,5-dicarboxylic acid 3-isopropyl ester 5-methyl ester], which has selective and long-acting cerebral vasodilator, cerebral circulation ameliorant and peripheral vasodilator activities.

Because of the above-mentioned excellent pharmacological activities, NB-818 and its optical isomer i.e. NB-818 optical isomer are being developed as drugs for the circulatory system, such as a hypotensive drug and an ameliorant of cerebral circulation. However, NB-818 and NB-818 optical isomer are extremely insoluble in water and hardly absorbable in the body after oral administration even in a finely pulverized form, not to mention a crystalline form, whereby no adequate pharmacological activities can be obtained.

Under these circumstances, it is strongly desired to improve their absorption by developing a suitable drug formulation. Heretofore, as a method of improving the absorption of a poorly soluble substance, it is known to dissolve the poorly soluble substance in polyethylene glycol 400 and filling the solution in capsules (see Japanese Unexamined Patent Publication No. 2861/1973). It has also been reported that a solid dispersion obtained by incorporating a poorly soluble substance in a polymer such as polyvinylpyrrolidone or methyl cellulose, has high bioavailability (Japanese Unexamined Patent Publication No. 46837/1979). However, the former method for capsule formulation has a drawback that since the capsule is a soft gelatin capsule type, its shape is obliged to be relatively large by the restrictions from the formulation process, and the formed capsule can hardly be administered. Whereas, the latter method provides high bioavailablity when the poorly soluble substance is contained in a small amount. However, when such a poorly soluble substance is contained in a large amount (at a level of from 5 to 15% by weight relative to the total amount of the solid dispersion granules), the layer of a polymer such as polyvinylpyrrolidone or methyl cellulose which has no function of improving the disintegration, is obliged to be thick, and the dissolution rate of such a polymer layer is slow, whereby it is difficult to obtain adequate effects for improving the absorption. Under the circumstances, it is desired to develop a drug formulation of solid dispersion granules containing a large amount of the poorly soluble substance and having a high dissolution rate from the viewpoint of the safety, the productivity and the nature of a drug for oral administration.

Solid dispersion granules containing a large amount of a poorly soluble substance have their surface coated with a large amount of a polymer. Therefore, even if a small amount (from 5 to 30% by weight relative to the total weight) of a binder commonly used for drug formulation, is incorporated, followed by compression molding, adequate hardness for practical use can not be obtained. In order to obtain adequate hardness, it is required to add the binder in a large amount. However, an addition of a large amount of the binder is undesirable from the viewpoint of the safety, the productivity and the nature of a drug for oral administration. Accordingly, it is desired to develop a method of obtaining adequate hardness with a small amount of a binder.

Further, the tablets obtained by compression molding of polymer solid dispersion granules of a poorly soluble drug such as NB-818 or NB-818 optical isomer, are required to show fast disintegration in order to attain good absorption as well as adequate hardness. However, when a water-soluble polymer is used alone as the polymer, the surface of the polymer granules tends to be gelled with water, whereby granules tend to adhere one another to form a matrix, and it takes time for water to penetrate into the matrix. Thus, it takes a long time for disintegration, the elution tends to be substantially delayed, and no adequate improvement in the absorption will be obtained. Even if a disintegrant is incorporated in a usual method in a usual amount (from 5 to 30% by weight relative to the total weight) to improve the disintegration, followed by compression molding, no adequate disintegration is obtainable. Therefore, it is desired to develop a new method for drug formulation.

It is an object of the present invention to provide a method of improving, by a new drug formulation, the absorption of NB-818 or NB-818 optical isomer which is extremely insoluble and poorly absorbable in the body either in a crystalline form or in a finely pulverized form and thereby to obtain adequate pharmacological effects. Another object of the invention is to provide a readily absorbable solid dispersion of NB-818 or NB-818 optical isomer, a tablet formulation containing it and a method for the preparation thereof.

The present invention provides a readily absorbable drug formulation of NB-818 or NB-818 optical isomer useful as a circulatory drug, such as a hypotensive drug or an ameliorant of cerebral circulation, and a method for its preparation.

Namely, the present invention provides a readily absorbable drug formulation obtained by incorporating both a nonionic surfactant and NB-818 or NB-818 optical isomer to a water-soluble or enteric polymer.

Now, the present invention will be described in detail with reference to the preferred embodiments.

The present invention comprises a step of dissolving specific proportions of NB-818 or NB-818 optical isomer, a nonionic surfactant and a water-soluble or enteric polymer in an organic solvent or in a water-containing organic solvent, a step of uniformly coating this solution on the surface of a carrier as nuclei to obtain solid dispersion granules, and a step of adding additives such as a binder and a disintegrator to the solid dispersion granules and preparing tablets.

The solution to be used for coating the above-mentioned solid dispersion containing NB-818 or NB-818 optical isomer on the surface of a carrier as nuclei such as an excipient, can be prepared by dissolving NB-818 or NB-818 optical isomer, a nonionic surfactant and a water-soluble or enteric polymer in a suitable organic solvent or in a water-containing organic solvent.

Suitable examples of the nonionic surfactant to be used here, include surfactants such as sucrose fatty acid ester, glycerin fatty acid ester, glyceryl monostearate, acetylated glycerin stearic acid ester, acetylated glycerin fatty acid ester, sorbitan fatty acid ester, sorbitan monolaurate, sorbitan sesquioleate, sorbitan monooleate, sorbitan trioleate and polyoxyl 40 stearate. Preferably, a nonionic surfactant with the hydrophile-lipophile balance (HLB) being about 15, such as RYOTO sugar ester P-1670 (sucrose fatty acid ester) manufactured by Mitsubishi Kasei Shokuhin Co., Ltd., may be mentioned.

The amount of the nonionic surfactant is usually from 0.1 to 3.0 parts by weight, preferably from 0.5 to 2.0 parts by weight relative to 1 part by weight of NB-818 or NB-818 optical isomer. The dissolution rate can be adjusted by the amount of the surfactant. Accordingly, it is thereby possible to prepare a sustained-release dosage form.

Suitable examples of the water-soluble or enteric polymer to be used, include hydroxypropylmethylcellulose (HPMC), methylcellulose (MC), polyvinylpyrrolidone (PVP), hydroxypropylmethylcellulose phthalate (HPMCP), carboxymethylethylcellulose (CMEC) and a methyl acrylate.methacrylic acid copolymer (Eudragit). These polymers may be used alone or, if necessary, in combination as a mixture of two or more.

The amount of such a polymer is usually from 0.2 to 5.0 parts by weight, preferably from 1.0 to 4.0 parts by weight, relative to 1 part by weight of NB-818 or NB-818 optical isomer.

There is no particular restriction as to the solvent to be used so long as it is capable of dissolving NB-818 or NB-818 optical isomer, the polymer and the surfactant. The amount may optionally be selected within the range sufficient to dissolve them. Usually organic solvents such as methyl alcohol, ethyl alcohol, dichloromethane, acetone and chloroform are used alone or in combination as a mixture of two or more. Further, a small amount (from 2 to 10% by weight) of water not to precipitate NB-818 or NB-818 optical isomer, may be added to reduce generation of static electricity, whereby the operation efficiency can be improved.

Solid dispersion granules can be prepared by uniformly coating the solution thus prepared on the surface of a carrier as nuclei by a method commonly used in the pharmaceutical field. As the carrier to be used here, an excipient commonly employed for drug formulation can be used. For example, lactose, starch, sucrose, crystalline cellulose, potassium hydrogen phosphate, partially gelatinized starch (PCS ®), low substituted hydroxypropyl cellulose (L-HPC ®), carboxymethyl cellulose calcium, croscarmellose sodium A type (Ac-Di-Sol ®), synthetic aluminum silicate, anhydrous silicic acid and magnesium alumino-methasilicate, may be used alone or in combination of two or more, as case requires. As the method for preparation, any conventional method commonly employed in the field of drug formulation may be employed so long as the solution is thereby uniformly coated on the surface of the carrier as nuclei. For example, there are methods employing apparatus such as a centrifugal flow-type granulator, a fluidized bed granulator, a rotary fluidized bed granulator, a reflux type fluidized bed granulator and a vacuum granulator. Preferred are method employing a fluidized bed granulator and a vacuum granulation drying coating apparatus. More specifically, it is preferred that in the same manner as in the conventional production of granules, a solution containing of NB-818 or NB-818 optical isomer, the surfactant and the polymer, is spray-coated to the carrier as nuclei in the fluidized bed granulator or in the vacuum granulation drying coating apparatus. The granules comprising the solid dispersion containing NB-818 or NB-818 optical isomer of the present invention, are characterized in that as shown in the Test Examples given hereinafter, a nonionic surfactant is incorporated in addition to the water-soluble or enteric polymer. By this feature, it is possible to improve the disintegration of the polymer layer and to provide a dissolution rate substantially higher than the conventional solid dispersion granules having only the polymer incorporated, in spite of the high content of NB-818 or NB-818 optical isomer.

The NB-818 or NB 818 optical isomer-containing solid dispersion granules prepared by the above method can be formed into tablets having adequate hardness by incorporating from 0.5 to 5% by weight, based on the total amount, of a binder, followed by compression molding by a conventional method. As the binder, light anhydrous silicic acid, magnesium alumino-methasilicate, magnesium alumino-silicate, aluminum hydroxide, synthetic hydrotalcite, finely pulverized titanium dioxide and aluminum silicate may be used alone or in combination as a mixture of two or more, as the case requires. Namely, with the NB-818 or NB-818 optical isomer-containing solid dispersion granules with the surface coated with a large amount of the polymer, practically durable hardness can not be obtained even if commonly employed micro-crystalline cellulose or the like is incorporated as the binder in an amount of from 5 to 30% by weight, based on the total weight, followed by compression molding. Adequate hardness can be obtained for the first time by the method of the present invention characterized in the incorporation of the above-mentioned binder.

At the time of tabletting the above NB-818 or NB-818 optical isomer-containing solid dispersion, a disintegrant may be added in addition to the above binder, to facilitate the disintegration and dispersion.

When a water-soluble polymer (such as HPMC, MC or PVP) is used as the polymer, the water-soluble polymer tends to be gelled, and the granules tend to adhere to one another to form a matrix, whereby the time required for disintegration tends to be prolonged, and the dissolution tends to be delayed, leading to poor absorption of the drug. In such a case, it is particularly advisable to incorporate a suitable disintegrant.

The tablets having solved the above problem involved in the use of a water-soluble polymer, can be prepared by incorporating at least two types of disintegrants selected from the group consisting of a disintegrant of swellable type capable of forming a stress in the interior of a solid formulation, a disintegrant having a nature of a binder and capable of providing a disintegrating effect by the surface tension of water penetrated into the interior of a solid formulation from the spaces among the particles and a disintegrant having the properties of the two preceeding disintegrants.

As the disintegrant of swellable type capable of forming a stress in the interior of a solid formulation to be used for the preparation of the tablets of the present invention, croscarmellose A-type (Ac-Di-Sol ®), carboxymethyl cellulose calcium (ECG-505 ®) and sodium carboxymethylstarch (Explotab ®, Primojel ®) may be mentioned. As the disintegrant having a nature of a binder and capable of providing a disintegrating effect by the surface tension of water penetrated through the spaces among the particles into the interior of a solid formulation, corn starch, hydroxypropyl starch (HPS ®), a partially gelatinized starch (PCS ®) and a product obtained by spray-drying a slurry mixture of HPS/synthetic aluminum silicate/micro-crystalline cellulose=3/1/1 (Perfiller-101 ®) may be mentioned. Further, as the disintegrant having the properties of such two disintegrants, low substituted hydroxypropyl cellulose (L-HPC ®) and polyvinylpolypyrrolidone (PVPP ®) may be mentioned. When these disintegrants are incorporated for tabletting, the amount of the disintegrants used is preferably from 5 to 35% by weight, relative to the total amount. The blending ratio of each disintegrant is preferably from 0.3 to 1 when two types of disintegrants having different properties are used. Likewise, the blending ratio of each disintegrant is preferably from 0.1 to 1 when at least three types of disintegrants having different properties are used. However, in addition to the main disintegrants, a small amount of other disintegrants may of course be incorporated. As an example of a preferred combination of disintegrants, a combination may be mentioned in which Ac-Di-Sol, L-HPC (LH-11) and Perfiller-101 are mixed in the proportions of from 0.5 to 1:from 0.5 to 1:from 0.5 to 1.

To the solid dispersion granules and tablets of the present invention, additives for drug formulation such as a colorant agent, a corrigent, flavor, a stabilizer, an antistatic agent and a diluent may be incorporated. Therefore, the present invention includes NB-818 or NB-818 optical isomer drug formulations having such additives incorporated therein.

Namely, the present invention has been accomplished on the basis of a discovery that solid dispersion granules comprising extremely insoluble NB-818 or NB-818 optical isomer, a nonionic surfactant and a water-soluble or enteric polymer in the above-mentioned proportions, readily dissolve and exhibit excellent absorption in spite of a high content of NB-818 or NB-818 optical isomer and further that tablets obtained by incorporating at least two types of disintegrants having different properties among the above-mentioned three types of disintegrants having different properties, in the above-mentioned proportions to said solid dispersion granules, followed by compression molding, have excellent moldability and disintegration and exhibit excellent absorption. The tablet formulation of the present invention is effective particularly when a water-soluble polymer is employed. However, the tablet formulation of the present invention designed to have the disintegration improved, is of course effective also when enteric polymer is employed.

Now, referring to Text Examples, the dissolution test method of NB-818 or NB 818 optical isomer, the method for measuring the concentration of NB-818 or NB-818 optical isomer in blood and the results thereof will be described.

The Dissolution Test

The test was conducted in accordance with the method 2 (paddle method) of a dissolution test method among general tests of the 11th Edition of Japanese Pharmacopia (JPXI). Namely, 100 mg of solid dispersion granules (containing 10 mg of NB-818 or NB-818 optical isomer) or 1 tablet (containing 10 mg of NB-818 or NB-818 optical isomer) was subjected to an dissolution test at 100 rpm by means of an dissolution tester (MW-1120 A-1 Model, manufactured by Hanson Research) prescribed in JPXI while maintaining either one of 500 ml of water (Test Example 1), 500 ml of the first fluid of JPXI (Test Examples 2 and 5) or 500 ml of the second fluid of JPXI (Text Example 3) as a test solution at a temperature of 37±0.5° C. The test solution was filtered through a miliporefilter (pore size: 0.8 μm), whereby the absorbance was continuously measured by a spectrophotometer (Hitachi 220A Model) by means of a flow cell, as the time passes. [Provided that a pelistar minipump (Minipuls 2-Model, manufactured by Gilson Company) was used in combination.]

TEST EXAMPLE 1

Figure 1:
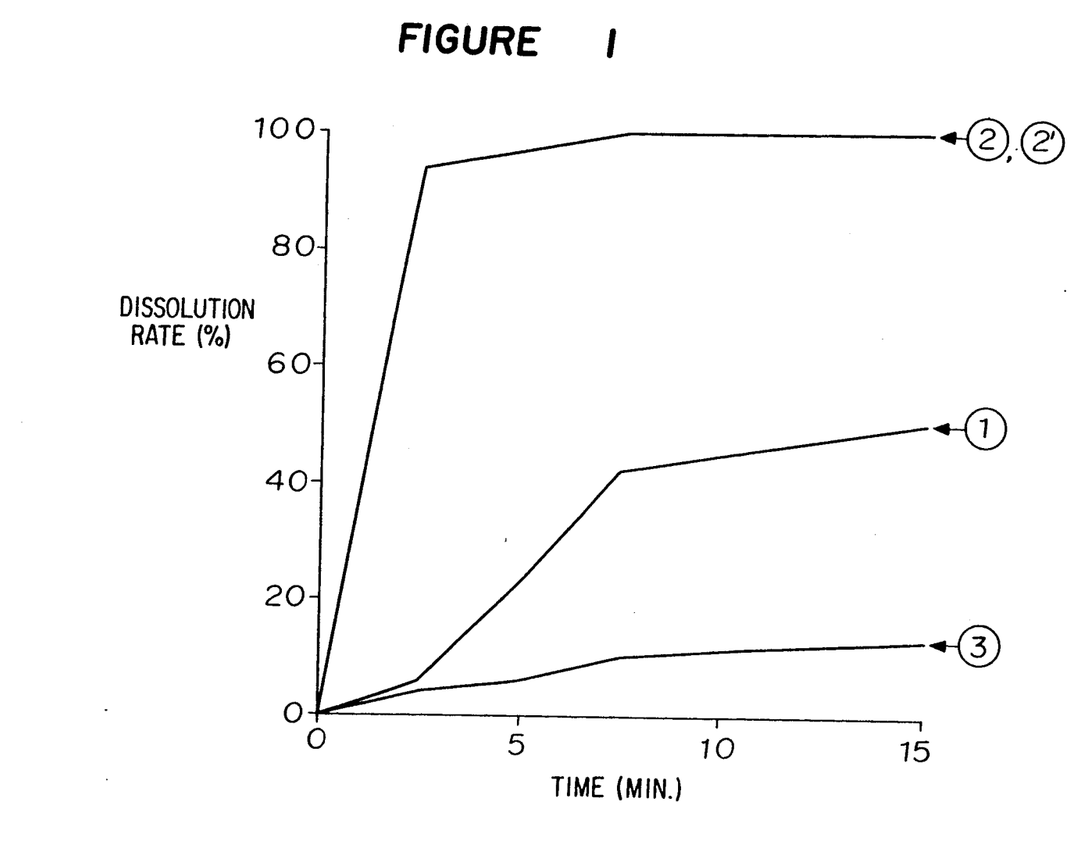
FIGS. 1 to 4 are graphs showing the results of dissolution tests of solid dispersion granules and tablets containing NB-818 or NB-818 optical isomer, wherein the ordinate indicates the dissolution rate of NB-818 or NB-818 optical isomer, and the abscissa indicates the time (minutes).

With respect to the formulations of Example 1 (curve ①), Example 2-a (curve ②), Example 2-b (curve ②') and Comparative Example 1 (curve ③), the dissolution test was conducted as described above. The results are shown in FIG. 1.

TEST EXAMPLE 2

With respect to the formulations of Example 2-a (curve ④), Example 3 (curve ⑤), Example 4 (curve ⑥), Example 5 (curve ⑦), Example 6 (curve ⑧) and Example 7 (curve ⑨), the dissolution test was conducted as described above. The results are shown in FIG. 2.

TEST EXAMPLE 3

With respect to the formulations of Example 2-a (curve ⑩), Example 3 (curve ⑪), Example 4 (curve ⑫), Example 5 (curve ⑬), Example 6 (curve ⑭) and Example 7 (curve ⑮), the dissolution test was conducted as described above. The results are shown in FIG. 3.

Figure 2:
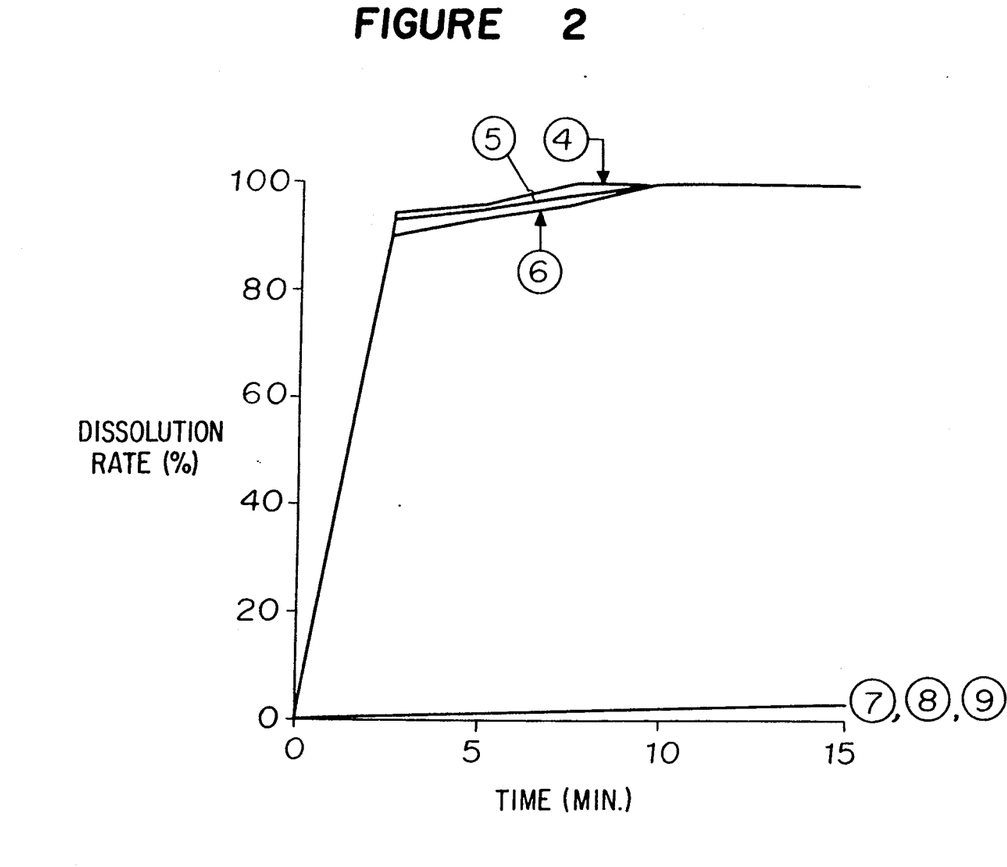
Figure 3:
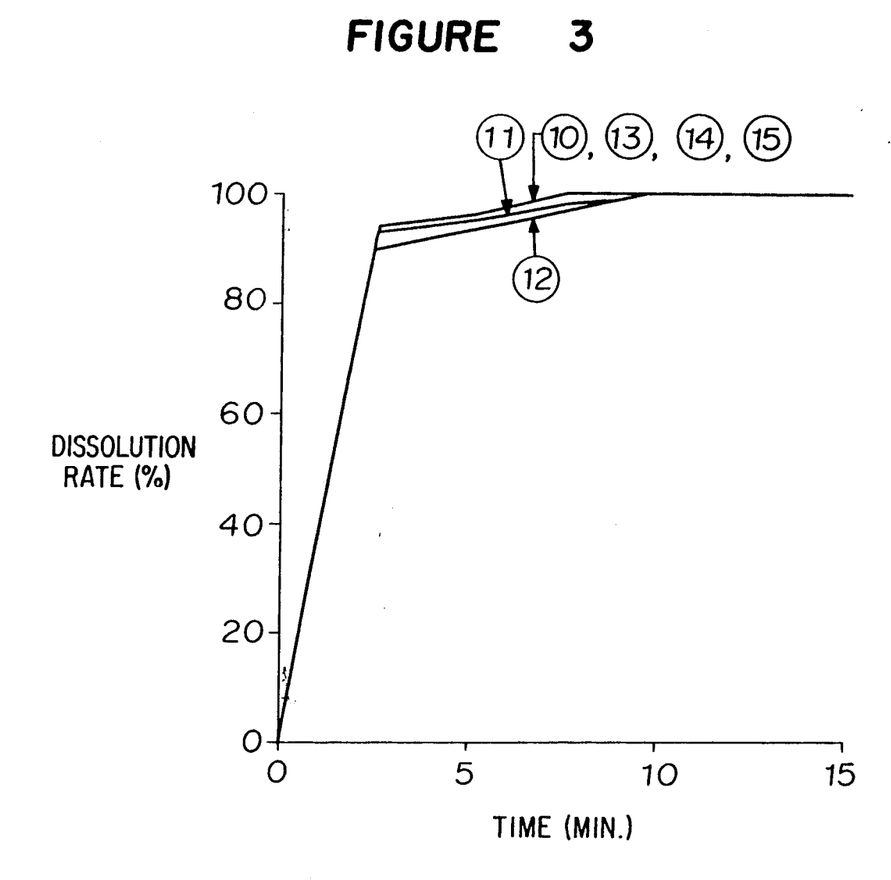

It is evident from FIGS. 1 to 3 that with the solid dispersion granules of the present invention, the dissolution rate is substantially large as compared with the solid dispersion granules of Comparative Example 1 wherein only the polymer was incorporated. It is thus apparent that to mix NB-818 or NB-818 optical isomer, the nonionic surfactant and the polymer in the above-mentioned specific proportions to obtain solid dispersion granules, is effective for improving the solubility and consequently the absorption. Further, the results indicate that the dissolution rate can be controlled by the amount of incorporation of the nonionic surfactant. Further, from Test Example 2 and 3, it is evident that when an enteric soluble polymer is used as the polymer, the solid dispersion granules undergo no substantial dissolution in the first fluid of JPXI and readily elute in the second fluid of JPXI, which indicates that the solid dispersion granules are not soluble in the stomach and readily dissolve when transferred to the intestines. This indicates that by a combination of solid dispersion granules using an enteric polymer and solid dispersion granules using a water-soluble polymer, it is possible to produce a sustained-release dosage form.

TEST EXAMPLE 4

With respect to the tablets of Examples 8 and 10 and Comparative Examples 2 and 3, evaluation of the hardness and the disintegration was conducted.

Hardness

The hardness of 10 tablets was measured by means of a balance-type hardness meter (2E/106 Model, manufactured by Sheroigel Company), and the average value was calculated.

Disintegration Test

The test was conducted in accordance with the disintegration test among the general tests of the 11th Edition of Japanese Pharmacopia. Namely, 6 tablets were put in glass tubes of the tester, (1 tablet in each tube), and reciprocated up and down in a predetermined amplitude in water at a temperature of 37°±0.5° C., whereby the time until disintegration was measured, and the average value was calculated.

|  | Hardness (kq) | Disintegration (min.) |
| --- | --- | --- |
| Example 8 | 6 | 6 |
| Example 10 | 8 | 3 |
| Comparative Example 2 | Less than 1 | —* |
| Comparative Example 3 | 5 | At least 30 |

*Not measured because the formulation did not have practically adequate hardness as tablets.

From the above results, it is evident that the tablets of the present invention are excellent in both the moldability and the disintegration (which are mutually opposing properties) as compared with the tablets (Comparative Examples 2 and 3) prepared by compression molding in accordance with a conventional method.

TEST EXAMPLE 5

Figure 4:
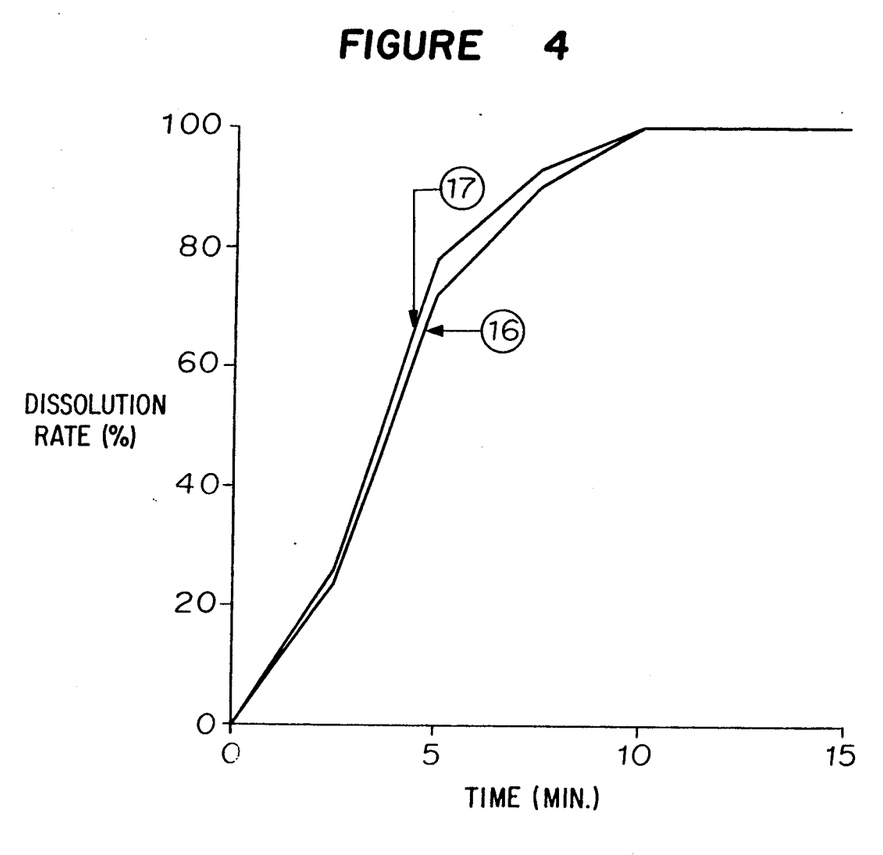

The test was conducted by the dissolution test as described above with respect to Example 8 (curve (16)) and Example 10 (curve (17)). As a results, the tablets of Examples 8 and 10 readily underwent dissolution as shown in FIG. 4. Thus, the tablets of the present invention showed excellent dissolution, which supports the excellent disintegration shown by the above Test Example 4.

TEST EXAMPLE 6

Figure 5:
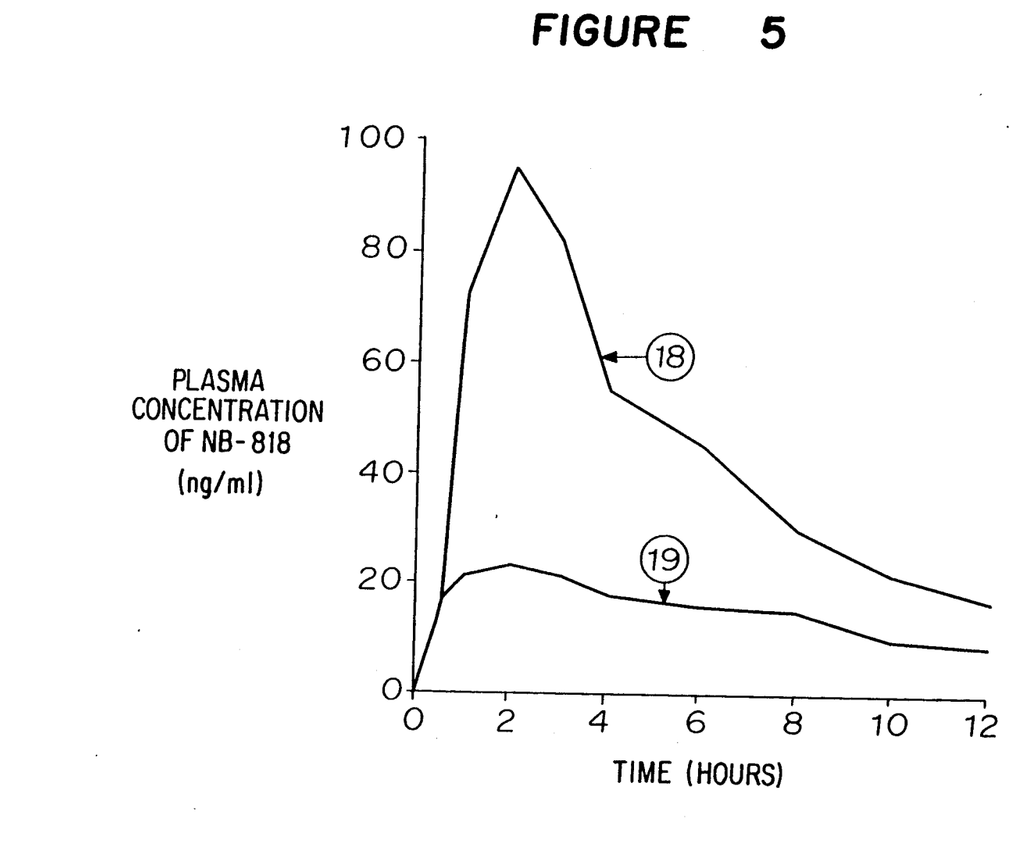
FIG. 5 is a graph showing the results of the absorption tests of the tablets of the present invention and comparative capsules, wherein the ordinate indicates the drug concentration (ng/ml) in the blood serum and the abscissa indicates the time (hours).

The tablets of Example 10 (curve (18)) and the capsules of Comparative Example 4 (curve (19)) were orally administered together with 50 ml of water (water was injected by a catheter) to male beagle dogs having a body weight of about 10 kg after fasting for 24 hours, whereupon the NB-818 concentration in blood serum was measured by a high performance liquid chromatography as the time passed. The results are shown in FIG. 5. As is evident from FIG. 5, there was a substantial improvement in the absorption.

Now, the present invention will be described in further detail with reference to Examples and Comparative Examples. However, it should be understood that the present invention is by no means restricted by these specific Examples.

EXAMPLE 1

500 g of NB-818, 500 g of RYOTO sugar ester (P-1670) and 1,500 g of HPMC 2910 (3cs) were dissolved in 30,000 g of a mixture of ethanol/dichloromethane/water (45/50/5). This solution was spray-coated on the surface of 2,500 g of lactose by means of a fluidized bed granulator (FLO-5 Model, manufactured by Freund Ind. Co., Ltd.).

EXAMPLE 2-a 500 g of NB-818, 1,000 g of RYOTO sugar ester (P-1670) and 1,500 g of HPMC 2910 (3 cs) were dissolved in 30,000 g of a mixture of ethanol/dichloromethane/water (45/50/5). This solution was spray-coated on the surface of 2,000 g of lactose by means of a fluidized bed granulator.

EXAMPLE 2-b

Granules containing NB-818 optical isomer were prepared in the same manner as in Example 2-a except that NB-818 optical isomer was used instead of NB-818.

EXAMPLE 3

500 g of NB-818, 1,000 g of RYOTO sugar ester (P-1670) and 1,500 g of MC (25cs) were dissolved in 30,000 g of a mixture of ethanol/dichloromethane/water (45/50/5). This solution was spray-coated on the surface of 2,000 g of lactose by means of a fluidized bed granulator.

EXAMPLE 4

500 g of NB-818, 1,000 g of RYOTO sugar ester (P-1670) and 1,500 g of PVP (K-30) were dissolved in 30,000 g of a mixture of ethanol/dichloromethane/water (45/50/5). This solution was spray-coated on the surface of 2,000 g of lactose by means of a fluidized bed granulator.

EXAMPLE 5

500 g of NB-818, 1,000 g of RYOTO sugar ester (P-1670) and 1,500 g of HPMCP 220824 (HP-50: enteric soluble polymer soluble at a pH of 5.0 or higher) were dissolved in 30,000 g of a mixture of ethanol/dichloromethane (1/1). This solution was spray-coated on the surface of 2,000 g of lactose by means of a fluidized bed granulator.

EXAMPLE 6

500 g of NB-818, 1,000 g of RYOTO sugar ester (P-1670) and 1,500 g of CMEC (enteric polymer) were dissolved in 30,000 g of a mixture of ethanol/dichloromethane (1/1). This solution was spray-coated on the surface of 2,000 g of lactose by means of a fluidized bed granulator.

EXAMPLE 7

500 g of NB-818, 1,000 g of RYOTO sugar ester (P-1670) and 1,500 g of Eudragit L (enteric polymer) were dissolved in 30,000 g of a mixture of ethanol/dichloromethane (1/1). This solution was spray-coated on the surface of 2,000 g of lactose by means of a fluidized bed granulator.

EXAMPLE 8

2,500 g of granules obtained in Example 2-a, 392 g of Ac-Di Sol, 391 g of L-HPC (LH-11), 392 g of lactose, 56.25 g of light anhydrous silicic acid and 18.75 g of magnesium.stearate, were uniformly mixed and then compressed by a conventional method to obtain tablets each having a weight of 150 mg and containing 10 mg of NB-818.

EXAMPLE 9

2,500 g of granules obtained in Example 1, 392 g of Ac-Di-Sol, 391 g of L-HPC (LH-11), 392 g of Perfiller, 56.25 g of light anhydrous silicic acid and 18.75 g of magnesium stearate, were uniformly mixed and then compressed by a conventional method into tablets each having a weight of 150 mg and containing 10 mg of NB-818.

EXAMPLE 10

2,500 g of granules obtained in Example 2-a, 392 g of Ac-Di-Sol, 391 g of L-HPC (LH-11), 392 g of Perfiller, 56.25 g of light anhydrous silicic acid and 18.75 g of magnesium stearate, were uniformly mixed and then compressed by a usual method into tablets each having a weight of 150 mg and containing 10 mg of NB-818.

EXAMPLE 11

2,500 g of granules obtained in Example 3, 392 g of Ac-Di-Sol, 391 g of L-HPC (LH-11), 392 g of Perfiller, 56.25 g of light anhydrous silicic acid and 18.75 g of magnesium stearate, were uniformly mixed and then compressed in accordance with a conventional method into tablets each having a weight of 150 mg and containing 10 mg of NB-818.

EXAMPLE 12

2,500 g of granules obtained in Example 5, 200 g of Ac-Di-Sol, 200 g of L-HPC (LH-11), 200 g of Perfiller, 52.5 g of light anhydrous silicic acid, 330 g of lactose and 17.5 g of magnesium stearate, were uniformly mixed and then compressed in accordance with a conventional method to obtain tablets each having a weight of 140 mg and containing 10 mg of NB-818.

COMPARATIVE EXAMPLE 1

500 g of NB-818 and 1,500 g of HPMC 2910 (3cs) were dissolved in 30,000 g of a mixture of ethanol/dichloromethane/water (45/50/5). This solution was spray-coated on the surface of 3,000 g of lactose by means of a fluidized bed granulator.

COMPARATIVE EXAMPLE 2

2,500 g of granules obtained in Example 2-a, 875 g of micro-crystalline cellulose (Avicel PH301, manufactured by Asahi Chemical Industries Co., Ltd.), 356.25 g of lactose and 18.75 g of magnesium stearate were uniformly mixed and then compressed in accordance with a conventional method to obtain tablets each having a weight of 150 mg and containing 10 mg of NB-818.

COMPARATIVE EXAMPLE 3

2,500 g of granules obtained in Example 2-a, 700 g of Ac-Di-Sol, 475 g of lactose, 56.25 g of light anhydrous silicic acid and 18.75 g of magnesium stearate were uniformly mixed and compressed in accordance with a conventional method to obtain tablets each having a weight of 150 mg and containing 10 mg of NB-818.

COMPARATIVE EXAMPLE 4

NB-818 crystals were pulverized by a jet mill (manufactured by Tarbo Kogyo Co., Ltd.) to obtain fine powder of NB-818 having an average particle size of not larger than 1 μm. 30 mg of this fine powder was filled in capsules.

According to the present invention, absorption of NB-818 or NB-818 optical isomer, which is extremely insoluble and hardly absorbable in the body in either a crystalline form or a finely pulverized form to provide adequate pharmacological activities, can substantially be improved. Thus, the present invention is useful in the pharmaceutical field, particularly in the field of the prevention and curing of diseases of circulatory organs.

We claim:

1. An orally administratable drug formulation having effective bioavailability in a pharmacologically effective dosage comprising a water-soluble or enteric polymer, a nonionic surfactant and (±)-2-carbamoyloxymethyl-4-(2,3-dichlorophenyl)-6-methyl-1,4-dihydropyridine-3,5-dicarboxylic acid 3-isopropyl ester 5-methyl ester or (−)-2-carbamoyloxymethyl-4-(2,3-dichlorophenyl)-6-methyl-1,4-dihydropyridine-3,5-dicarboxylic acid 3-isopropyl ester 5-methyl ester.

2. The drug formulation according to claim 1, wherein the nonionic surfactant is at least one member of the group consisting of glycerin fatty acid ester, glyceryl monostearate, acetylated glycerin stearate, acetylated glycerin fatty acid ester, sorbitan fatty acid ester, sorbitan monlaurate, sorbitan sesquioleate, sorbitan monooleate, sorbitan trioleate, polyoxyl 40 stearate and sucrose fatty acid ester.

3. The drug formulation according to claim 1, wherein the water-soluble or enteric polymer is at least one member of the group consisting of hydroxypropylmethylcellulose, methylcellulose, polyvinylpyrrolidone, hydroxypropylmethylcellulose phthalate, a methyl acrylate.metacrylic acid copolymer, carboxymethylethylcellulose and cellulose acetate phthalate.

4. The drug formulation according to claim 1, which contains from 0.1 to 3.0 parts by weight of the nonionic surfactant and from 0.2 to 4.0 parts by weight of the water-soluble or enteric polymer, relative to 1 part by weight of (+)-2-carboxyoxymethyl-4-(2,3-dichlorophenyl)-6-methyl-1,4-dihydropyridine-3,5-dicarboxylic acid 3-isopropyl ester 5-methyl ester or (−)-2-carbamoyloxymethyl-4-(2,3-dichlorophenyl)-b 6-methyl-1,4-dihydropyridine-3,5-dicarboxylic acid 3-isopropyl ester 5-methyl ester.

5. A tablet formulation obtained by incorporating from 0.5 to 5.0% by weight, based on the total amount, of at least one member selected from the group consisting of light anhydrous silicic acid, magnesium aluminomethasilicate, magnesium alumino-silicate, aluminum hydroxide, synthetic hydrotalcite, fine titanium oxide and aluminum silicate, as a binder, to solid dispersion granules comprising a pharmacologically effective mixture of (±)-2-carboxyoxymethyl-4-(2,3-dichlorophenyl-6-methyl-1,4-dihydropyridine-3,5-dicarboxylic acid 3-isopropyl ester 5-methyl ester or (−)-2-carbamoyloxymethyl-4-(2,3-dichlorophenyl)-b 6methyl-1,4-dihydropyridine-3,5-dicarboxylic acid 3-isopropyl ester 5-methyl ester, a nonionic surfactant and a water-soluble or enteric polymer.

6. A tablet formulation obtained by incorporating from 5.0 to 35% by weight, based on the total amount, of at least one member selected from the group consisting of a swellable polymer disintegrant capable of forming stress in a solid formulation, a disintegrant having a nature of a binder and capable of providing a disintegrating effect by the surface tension of water penetrated into a solid formulation through the spaces among particles and a disintegrant having both of the above-mentioned properties, to solid dispersion granules comprising a pharmacologically effective mixture of (±)-2-carboxyoxymethyl-4-(2,3-dichlorophenyl-6-methyl-1,4- dihydropyridine-3,5-dicarboxylic acid 3-isopropyl ester 5-methyl ester or (−)-2-carbamoyloxymethyl-4-(2,3-dichlorophenyl)-b 6methyl-1,4-dihydropyridine-3,5-dicarboxylic acid 3-isopropyl ester 5-methyl ester, a nonionic surfactant and a water-soluble or enteric polymer.

7. A method for preparing solid dispersion granules, which comprise incorporating to a water-soluble or enteric polymer, both a nonionic surfactant and (±)-2-carboxyoxymethyl-4-(2,3-dichlorophenyl-3,5-dicarboxylic acid 3-isopropyl ester 5-methyl ester or (−)-2-carbamoyloxymethyl-4-(2,3-dichlorophenyl)-b 6methyl-1,4-dihydropyridine-3,5-dicarboxylic acid 3-isopropyl ester 5-methyl ester.

8. A method for preparing a tablet formulation, which comprises incorporating a binder as defined in claim 5 to solid dispersion granules comprising a pharmacologically effective amount of (±)-2-carboxyoxymethyl-4-(2,3-dichlorophenyl-6-methyl-1,4-dihydropyridine-3,5-dicarboxylic acid 3-isopropyl ester 5-methyl ester or (−)-2-carbamoyloxymethyl-4-(2,3-dichlorophenyl)-b 6methyl-1,4-dihydropyridine-3,5-dicarboxylic acid 3-isopropyl ester 5-methyl ester, a nonionic surfactant and a water-soluble or enteric polymer, followed by compression molding.

9. A method for preparing a tablet formulation, which comprises incorporating from 5.0 to 35% by weight, based on the total amount, of at least two disintegrants selected from a group consisting of a swellable polymer disintegrant capable of forming stress in a solid formulation, a disintegrant having a nature of a binder and capable of providing a disintegrating effect by the surface tension of water penetrated into a solid formulation through the spaces among particles and a disintegrant having such two types of properties, to solid dispersion granules comprising a pharmacologically effective mixture of (±)-2-carboxyoxymethyl-4-(2,3-dichlorophenyl-6-methyl-1,4-dihydropyridine-3,5-dicarboxylic acid 3-isopropyl ester 5-methyl ester or (−)-2-carbamoyloxymethyl-4-(2,3-dichlorophenyl)-b 6methyl-1,4-dihydropyridine-3,5-dicarboxylic acid 3-isopropyl ester 5-methyl ester, a nonionic surfactant and a water-soluble or enteric polymer, followed by compression molding.

\* \* \* \* \*